US005221251A

United States Patent [19]
Edminster

[11] Patent Number: 5,221,251
[45] Date of Patent: Jun. 22, 1993

[54] PENILE ERECTION SUSTAINER

[76] Inventor: Robert E. Edminster, 7698 E. Minnezona Ave., Scottsdale, Ariz. 85251

[21] Appl. No.: 848,715

[22] Filed: Mar. 9, 1992

[51] Int. Cl.$^5$ .................................................. A61F 5/41
[52] U.S. Cl. ................................................................ 600/41
[58] Field of Search ................................ 600/38, 39, 41; 606/201; 128/876, 883, 885, DIG. 15; 24/68 BT, 68 ST

[56]  References Cited

U.S. PATENT DOCUMENTS

| 3,376,865 | 4/1968 | Gamper | 128/DIG. 15 |
| 3,773,040 | 11/1973 | Gavrilovich | 128/79 |
| 3,845,760 | 11/1974 | Birman | 128/79 |
| 4,273,130 | 6/1981 | Simpson | 128/DIG. 15 |
| 4,539,980 | 9/1985 | Chaney | 128/79 |
| 4,723,538 | 2/1988 | Stewart et al. | 128/79 |
| 4,834,115 | 5/1989 | Stewart | 128/842 |
| 4,856,498 | 8/1989 | Oslon | 128/79 |
| 5,027,800 | 7/1991 | Rowland | 128/79 |
| 5,063,915 | 11/1991 | Wyckoff | 600/38 |
| 5,085,209 | 2/1992 | Gottschalk | 600/41 |

Primary Examiner—Cary E. O'Connor

[57] ABSTRACT

A penile erection sustainer for assisting in obtaining and sustaining a human penile erection. The sustainer provides a remote, quick release adjustable method for restricting blood flow from the penis. In the preferred embodiment, a soft pliable fabric ribbon member is used to encircle the penis. A hook and loop pile fastener of sufficient length and correct placement adapts the sustainer to varying penis sizes. Attached to the encircling end of the ribbon member are unique twin narrow ribbon tightening members. They are used to tighten the sustainer around the penis. They do not interfere with the release of the sustainer. No elastic components or materials are used in the sustainer. An extended length of the ribbon member is used to remotely release the sustainer without disturbing the act. A quick release permits unrestricted ejaculation. A soft protective cover protects from irritation by the hook portion of the fastener if the sustainer is fully withdrawn while the participants are in close body contact. Complete removal of the sustainer from the penis is not required at release. Use of synthetic materials and flexible waterproof adhesive assure a long lasting and machine washable unit.

2 Claims, 1 Drawing Sheet

PENILE ERECTION SUSTAINER

BACKGROUND—FIELD OF INVENTION

This invention relates to impotency problems and a device that assists in obtaining and sustaining an erection for sexual intercourse.

BACKGROUND AND DISADVANTAGES OF PRIOR ART

Impotency, the inability to perform sexual intercourse, is a severe psychological and/or physiological problem for many men. Men of all ages are affected. It can be very traumatizing and cause depression and marital discord. A man's feelings of self worth, competence and masculinity are definitely related to his sexual functioning.

When an erection occurs naturally, the arteries supply blood to two sponge like lengthwise cavities in the penis. Sufficient blood flow expands these cavities. The cavities then press outwards on veins near the surface of the penis. This restricts the veins, reducing the flow of blood from the penis. This sustains the erection.

Impotency occurs when the blood flow to the penis is not adequate. The blood flow does not exert sufficient pressure in the cavities to restrict the veins. An erection may not be attained at all or it is lost before intercourse can be completed.

For many men the erection may be sustained by the use of an entrapment device. These devices are also called constriction rings. The use of an entrapment device is usually preferred instead of the use of a penile implant. A penile implant requires surgery. It is used where physical problems prevent blood flow to the penis for an erection. An entrapment device encircles the penis close to the body and puts pressure on the veins. This restricts the flow of blood from the penis. It sustains the erection provided sufficient blood enters the penis.

Sufficient blood for an erection occurs when:
1. a man initially achieves a normal erection, or
2. a vacuum device, widely prescribed by physicians, is placed over the penis to pull blood into it, or
3. the artery at the base of the penis behind the scrotum is pressed and firmly stroked towards the penis, bringing blood into the penis.

In all three cases, an entrapment device may be used to restrict the flow of blood from the penis. This sustains the erection.

Prior art suffers from many disadvantages. Some of these disadvantages are:

(a) Exact size required

Constriction rings are usually sold in sets so the proper size can be selected. Too small restricts blood flow to the penis, Too large won't restrict blood flow from the penis.

(b) Assessories required

Rings require stretching to be put in position. Cones and sleeves are sold for this purpose.

(c) Distracting placement

Use of stretching and positioning paraphennalia may spoil the romantic mood.

(d) Discomfort

Many rubber rings have small cross sections giving high localized pressure. This pressure tends to be uncomfortable and may irritate or damage the penis.

(e) Awkward removal

To properly ejaculate, the entrapment device must be stretched or removed. To reach the device for stretching or removal disturbs the closeness and finality of the act.

(f) Limited life

Many rubber compounds used for rings are affected chemically by lubricants used for intercourse. They decompose and may only last a few months.

(g) Cost

Many rings are sold as sets to select the proper size. Mounting or release assessories may also be required. These sets and assessories are expensive.

OBJECTS AND ADVANTAGES

The present invention, a penile erection sustainer, evolved from the need to restrict the blood flow from the penis but not have the disadvantages of the prior art. Accordingly, several objects and advantages of the presented invention are:

(a) to provide a sustainer without the use and disadvantages of elastic components or materials:

(b) to provide a sustainer that may be tightened around the penis with a consistent snug fit without concern for selected pressures or adjustments:

(c) to provide a sustainer that has a hook and loop pile fastener for ease of attachement, adjustability, and detachment;

(d) to provide a sustainer that has a protective cover which covers the hook portion of the fastener at release and removal:

(e) to provide a sustainer that exerts sufficient pressure to restrict blood flow from the penis but does not prevent blood flow to the penis:

(f) to provide a sustainer that uses a tightening method that is simple and unobtrusive yet does not interfere with the release or removal of the sustainer;

(g) to provide a sustainer that has sufficient contact area to be comfortable and does not cause localized high pressure with possible irritation or injury;

(h) to provide a sustainer that may be quickly released at ejaculation;

(i) to provide a sustainer that may be remotely released and removed without disturbing the participants in close body contact, especially when the woman is on top and the man has minimal reaching access;

(j) to provide a sustainer that does not require a selection of sizes for use;

(k) to provide a sustainer that does not spoil the romantic mood by use of mounting or positioning accessories;

(l) to provide a sustainer that may be readily placed in position on the penis in the dark and under bed covers;

(m) to provide a sustainer that may be positioned on the penis before use of a vacuum device to aid in attaining and sustaining an erection;

(n) to provide a sustainer of soft, pliable, synthetic materials not affected by lubricants or washing;

(o) to provide a sustainer at low cost without need for a selection of sizes or use of pherepheral equipment or accessories.

Further objects and advantages will become apparent from a consideration of the ensuing description and drawing.

DESCRIPTION OF THE DRAWING

A preferred embodiment of this invention is shown in the accompanying drawing.

For clarity, components are shown not to scale and bulkier than actual size. FIG. 2 and FIG. 3 show the sustainer encircling the penis such that the extended length is placed to the left for use. A right handed person would probably reverse the direction of encirclement.

REFERENCE NUMERALS IN DRAWING

- 10 penile erection sustainer
- 12 ribbon member
- 14 extended length
- 16 encircling end
- 18 outer surface
- 20 inner surface
- 22 tightening member
- 24 tightening member
- 26 termination feature
- 28 termination feature
- 30 termination feature
- 32 hook portion
- 34 loop pile portion
- 36 protective cover.

DESCRIPTION OF THE PREFERRED EMBODIMENT

Figure 1:
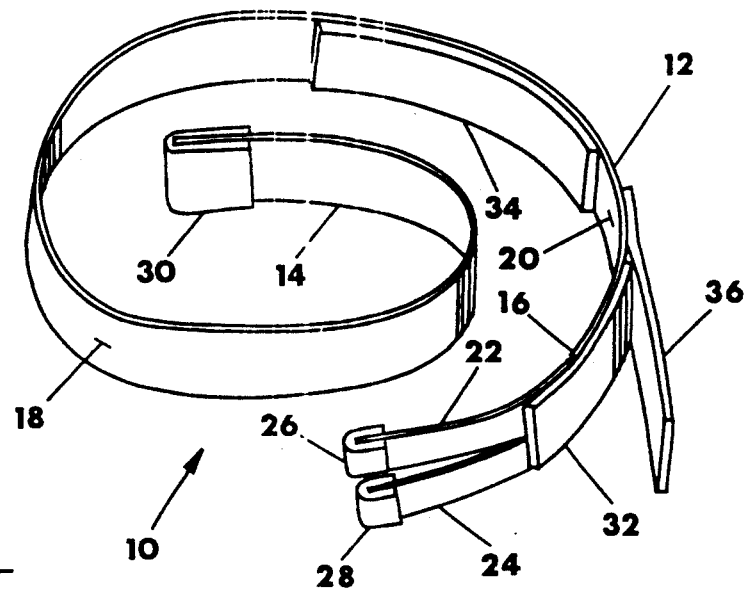
FIG. 1 is a perspective view in a free state showing all components of the sustainer.

Referring to the drawing and particularly to FIG. 1, there is shown a penile erection sustainer 10. The sustainer 10 includes a ribbon member 12 that is used to encircle a penis. The ribbon member 12 has an extended length 14 that does not encircle the penis. It is grasped and pulled to remotely release the sustainer 10 without disturbing the close body contact of the man and woman. Termination feature 30 facilitates grasping and pulling the extended length 14.

A hook portion 32 of a hook and loop pile fastener is attached to the outer surface 18 of ribbon member 12 such that it extends beyond the encircling end 16 of ribbon member 12. Two identical narrow ribbon tightening members 22 and 24 are attached in parallel to the extended underneath side of the hook portion 32. They project from the end of the hook portion 32. These tightening members 22 and 24 have identical termination features 26 and 28, respectively. They are used to facilitate grasping and pulling the tightening members 22 and 24. A loop pile portion 34 of a hook and loop pile fastener is attached to the inner surface 20 of ribbon number 12. The loop pile portion is of sufficient length and correct placement to permit attachment to hook portion 32 when varying penis sizes are encircled. A soft, pliable protective cover 36 is attached to the outer surface 18 of ribbon member 12 such that it overlaps to cover hook portion 32.

In the preferred embodiment, the ribbon member 12 is a durable but pliable polyester ribbon. It is 1.57 cm (0.63") wide by 0.3 mm (0.012") thick with woven edges. Common decorative ribbon is only one half the thickness and does not have a woven edge. The tightening members 22 and 24 are of the same material and thickness but only 0.6 cm (0.25") wide. The hook portion 32 and the loop pile portion 34 are the same width as the ribbon member 12. The protective cover 36 is loop pile and also the same width as the ribbon member 12. Loop pile is folded and cemented around the ends of the tightening members 22 and 24 and the end of the extended length 14 to become termination features 26, 28 and 30 respectively. The hook portion 32 and all loop pile are of nylon with pliable backing. They are attached with waterproof flexible adhesive.

Figure 2:
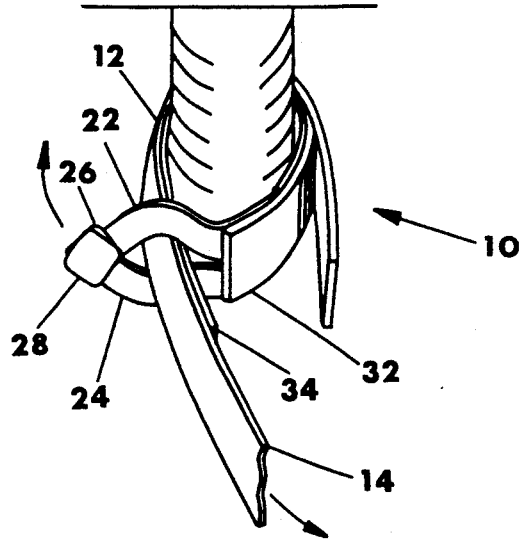
FIG. 2 is a perspective view showing how the tightening members (22 and 24) are utilized.

FIG. 2 shows the tightening members 22 and 24 and their termination features 26 and 28 respectively. The penis has been encircled and the extended length 14 positioned as shown. It is gripped closely to the loop pile portion 34 by the right hand. Tightening member 22 is brought over ribbon member 12 and tightening member 24 is brought under ribbon member 12. The termination features 26 and 28 of tightening members 22 and 24 respectively are held together with the left hand's forefinger and thumb. By pulling the tightening members 22 and 24 around the penis in a clockwise direction and pulling the extended length 14 counterclockwise around the penis, tightening of the sustainer 10 is accomplished. The loop pile portion 34 is pressed firmly against the hook portion 32 with the protective cover 36 aside. The extended length 14 is positioned to the left in preparation for remote release of the sustainer 10.

Figure 3:
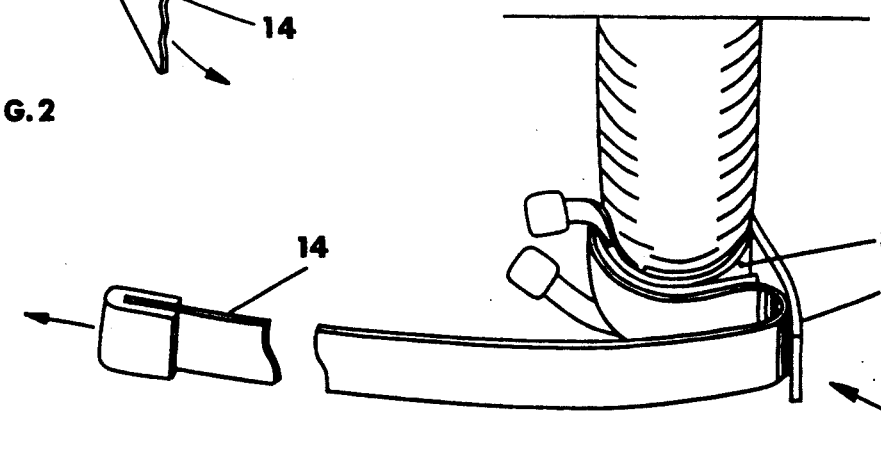
FIG. 3 is a perspective view of the sustainer tightened in position.

FIG. 3 shows the sustainer 10 after being tightened. It is restricting the flow of blood from the penis, sustaining the erection. The sustainer 10 may be immediately released by a tug on the extended length 14. Full removal of the sustainer 10 is not necessary at release. If the sustainer 10 is removed, the protective cover 36 prevents exposure of the hook portion 32 and possible body irritation.

SUMMARY, RAMIFICATIONS AND SCOPE

Accordingly, the reader will see that this invention, a penile erection sustainer, has many advantages over prior art. It solves the need for a penile erection sustainer that is simple and economical yet accomplishes much that prior art does not do. It is not like a traditional constriction ring that requires a selection of sizes, that is difficult to release for ejaculation and is difficult to remove. The sustainer may be readily put in place without accessories. Without elastics, a comfortable repeatably consistent snug fit can be attained without the problems of selected pressures or adjustments. A unique tightening method permits this proper fit yet permits a quick release and removal. The use of a hook and loop pile fastener is used for ease of attachment, adjustability and quick detachment. By extending the encircling ribbon as shown in the drawing of the preferred embodiment, a remote quick release and removal at ejaculation is possible. This may be accomplished while the couple are in close body contact, not possible with prior art. A protective cover over the hook portion of the fastener prevents possible irritation at removal.

Although the description above contains many specificities, these should not be construed as limiting the scope of the invention but as merely providing illustration of a preferred embodiment of this invention. For example, the size, shape and materials may be changed yet still accomplish the stated advantages. The method of attachment may be done by sewing, heat fusion, or other ways, rather than adhesive. The termination features may be made by folding and stitching or attachments instead of using loop pile.

Thus the scope of the invention should be determined by the appended claims and their legal equivalents, rather than by the examples given.

I claim:

1. A penile erection sustainer for assisting in obtaining and sustaining a human penile erection comprising: an elongate flexible strap having inner and outer ends releasably securable together to form a loop encircling the penis, wherein said inner end and said outer end having portions comprised of an interlocking material to interconnect said strap when so encircled, said inner end having two tightening members attached, said tightening members being of unobtrusive size yet adequate in strength for the tightening procedure, said tightening members of sufficient length to be brought one to each side of said outer end and both grasped by one hand, said sustainer being tightened by pulling on said tightening members with said one hand as the other hand pulls on said outer end, said outer end overlapping said inner end, fastening the interlocking material.

2. The penile erection sustainer of claim 1 further including a protective flap over the potentially physically irritating portion of the interlocking material, said protective flap moved aside when the interlocking material is fastened.

* * * * *